US006853310B2

(12) United States Patent
Brinsfield (10) Patent No.: US 6,853,310 B2
(45) Date of Patent: Feb. 8, 2005

(54) TRI-MODE MEDICAL TELEMETRY ANTENNA SYSTEM

(75) Inventor: James W. Brinsfield, Mequon, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 563 days.

(21) Appl. No.: 09/683,059

(22) Filed: Nov. 14, 2001

(65) Prior Publication Data

US 2002/0095271 A1 Jul. 18, 2002

Related U.S. Application Data (63) Continuation-in-part of application No. 09/474,593, filed on Dec. 29, 1999, now Pat. No. 6,556,630.

(51) Int. Cl.[7] .............................................. H04L 27/16
(52) U.S. Cl. .......................... 340/870.41; 340/870.11; 340/825.49; 340/539.1; 340/539.13; 600/301; 455/188.1; 375/346
(58) Field of Search .................. 340/870.11, 870.41, 340/825.49, 539.1, 539.12, 539.13; 375/335, 349, 346; 455/188.1, 180.1; 600/509, 301

(56) References Cited

U.S. PATENT DOCUMENTS

| 3,639,907 | A | 2/1972 | Greatbatch |
| 4,658,831 | A | 4/1987 | Reinhard et al. |
| 4,675,656 | A | 6/1987 | Narcisse |
| 4,689,627 | A | 8/1987 | Lee et al. |
| 4,827,943 | A | 5/1989 | Bornn et al. |
| 4,958,645 | A | 9/1990 | Cadell et al. |
| 5,153,584 | A | 10/1992 | Engira |
| 5,205,294 | A | 4/1993 | Flach et al. |
| 5,319,363 | A | 6/1994 | Welch et al. |
| 5,396,224 | A | 3/1995 | Dukes et al. |
| 5,458,123 | A | 10/1995 | Unger |
| 5,579,001 | A | 11/1996 | Dempsey et al. |
| 5,579,775 | A | 12/1996 | Dempsey et al. |
| 5,687,734 | A | 11/1997 | Dempsey et al. |
| 5,694,940 | A | 12/1997 | Unger et al. |
| 5,855,550 | A | 1/1999 | Lai et al. |
| 6,556,630 | B1 * | 4/2003 | Brinsfield et al. .......... 375/335 |

* cited by examiner

Primary Examiner—Albert K. Wong
(74) Attorney, Agent, or Firm—Andrus, Sceales, Starke & Sawall, LLP (57) ABSTRACT

A tri-mode telemetry system useful for monitoring patients in a care unit of a health care facility. The system includes an antenna system with a first antenna tuned to receive a signal in a first communication band, a second antenna tuned to receive a signal in a second communication band, a third antenna tuned to receive data signals, a down converter for producing a frequency translation signal, and a mixer coupled to the second antenna. The mixer combines the signal received by the second antenna with the frequency translation signal to produce a signal having a frequency in the first communication band. A combiner coupled to the mixer and the first antenna combines the signal generated by the mixer with the signal received by the first antenna. The combined signals and data signals are delivered to a wiring system.

40 Claims, 4 Drawing Sheets

TRI-MODE MEDICAL TELEMETRY ANTENNA SYSTEM

CROSS REFERENCE TO RELATED APPLICATIONS

This application is a continuation-in-part of U.S. application Ser. No. 09/474,593, filed Dec. 29, 1999 now U.S. Pat. No. 6,556,630.

BACKGROUND OF INVENTION

The present invention relates to systems and devices for monitoring patients in a healthcare facility. More particularly, the invention relates to patient monitoring systems that allow the patient to ambulate through a care unit in the facility and that provide a high-speed data link for information management and other purposes.

Most patient monitoring systems that permit patients to ambulate through a care unit use telemetry-based communication schemes. In one common form, the patient wears a telemetry transmitter attached to the patient using ECG electrodes. The telemetry transmitter acquires an ECG signal, conducts a nominal amount of filtering on the ECG signal, and transmits a telemetry data signal to an antenna array, typically located in the ceiling of the care unit. The telemetry signal is conducted through the antenna array to a telemetry receiver, which in turn, is connected to a central station that analyzes and displays the ECG information for viewing and evaluation by the clinicians staffing the care units.

Existing medical telemetry systems are regulated by the Federal Communications Commission (FCC) and are authorized to use VHF (very high frequency) and UHF (ultra high frequency) radio-frequency (RF) bands for their wireless data links. Presently, it is necessary to install two separate telemetry infrastructures or systems to utilize both of these bands. Of course, installing two systems increases the cost of patient monitoring. Proposed changes in FCC regulations will provide a new band (the L-band) in the RF spectrum for medical telemetry systems. While the addition of the new band will provide new capacity for telemetry systems and help reduce interference with other RF signals, operating in the new band with current technology will require an additional and separate telemetry infrastructure.

In addition to the problems noted above, current telemetry systems are, in general, unable to support applications that require relatively high-speed data links. Such applications include bedside monitoring, telephony services, and image transfer services. If present at all, these services are generally implemented with high-bandwidth wired networks that are separate from currently used telemetry systems.

SUMMARY OF INVENTION

Accordingly, a system supporting telemetry as well as high-speed data transfers would be less costly than dual systems; one for telemetry and another for data transfer. Further, an integrated system would simplify problems associated with cluttered RF or wireless environments that are created when multiple disparate wireless systems are used.

The present invention provides a tri-mode telemetry system that is capable of supporting UHF and L-band signals as well as high-speed wireless data transfers. The architecture of the system permits the detection and processing of L-band, UHF, and high-speed data signals with a common antenna system, thereby eliminating costly, redundant infrastructure that would otherwise be required.

In one embodiment, the tri-mode telemetry system includes a first antenna tuned to receive a signal having a frequency in a first communication band; a second antenna tuned to receive a signal having a frequency in a second communication band; and a down converter for producing a frequency translation signal. A mixer is coupled to the second antenna and to the down converter such that the mixer uses the signal received by the second antenna and the frequency translation signal to produce a signal having a frequency in the first communication band. A combiner combines the signal having a frequency in the first communication band with the signal received by the first antenna and produces an output signal.

The system also includes a third antenna designed to receive a signal in a third communication band. A wireless access device is coupled to the third antenna and produces an output signal. The third antenna is designed to support applications that require relatively fast data transmission. Preferably, the third antenna and associated components are shielded from the first and second antennas and associated components such that the high-speed data transmissions do not interfere with the lower speed RF transmissions.

The high and low speed data may be transmitted in a single apparatus. In one embodiment, the tri-mode telemetry system includes a cable bundle adapter that is coupled to the combiner and the wireless access device. The adapter accepts a cable bundle having a first conductor conducting data in the first communication band and a second conductor conducting digital data. In this way, a single parallel wiring system that handles both types of signals may be installed, avoiding the need to route and install two separate wires or cables to handle both types of signals.

In another embodiment, the tri-mode telemetry system includes a mixed signal processor coupled to the combiner and the wireless access device. The mixed signal processor mixes the output signal of the wireless access device and the output signal of the combiner. In this case, the mixed signal may be carried by a single conductor, again reducing cable and wiring installation costs.

In yet another embodiment, the invention provides a method of monitoring patients in a care unit. The method includes acquiring a patient data signal from a first transmitter that operates in a first communication band; acquiring a patient data signal from a second transmitter that operates in a second communication band; and converting the patient data signal from the second transmitter to a third signal in the first communication band. The first and third signals are then combined and delivered to a receiver. A data signal is also acquired from a first data device, such as a bedside monitor, telephone system, imaging system or other device that requires a relatively high-speed data link. The first data device operates in a third communication band. The data acquired from the first data device is delivered to a second data device, such as a monitoring station.

One advantage of the present invention is that it eliminates the need to provide a receiver subsystem capable of processing signals in multiple frequency bands. The signal received by the second antenna is converted to a signal in the first frequency band and, thus, may be processed by the same receiver subsystem that processes signals from the first antenna.

The first antenna is designed to receive UHF signals and the second antenna is designed to receive L-band signals. The first antenna is designed to receive signals in a particular channel within the UHF band and the signals from the second antenna are converted in a down converter to a second channel in the UHF band before detection at the receiver station.

The down converter is designed so that the frequency of the translation signal may be selected so that the converted signal produced by the mixer falls within the second channel in the first frequency. The frequency of the second channel depends on factors such as avoiding interference with other RF signals including the signal from the first antenna and local UHF signals from television broadcasts. To set an appropriate frequency for the translation signal, the down converter uses an oscillator, a synthesizer, and a filter coupled in a series loop (i.e., the components form a phase-lock loop). The synthesizer is programmed through a microprocessor that can receive input from a technician, administrator, or similar person to adjust the frequency. The synthesizer derives its frequency reference from a temperature controlled oscillator to compensate for temperature changes.

The antenna system is designed to work with telemetry transmitters worn by patients in a care unit, a receiver subsystem, and a central station. The transmitters acquire patient data and transmit that data at a predetermined frequency. In its simplest form, the system operates with one telemetry transmitter that operates in the first frequency band and a second transmitter that operates in the second frequency band. The signals sent by the telemetry transmitters are received by the first and second antennas and the signal from the second antenna is converted as described above. The signal from the first antenna and the converted signal are then relayed to the receiver subsystem which in turn delivers the signals to a central station. The patient data is collected and analyzed at the central station.

As is apparent from the above, it is an advantage of the present invention to provide a multiple band telemetry system that handles data in multiple communication bands. Other features and advantages of the present invention will become apparent by consideration of the detailed description and accompanying drawings.

DETAILED DESCRIPTION

Before embodiments of the invention are explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

Figure 1:
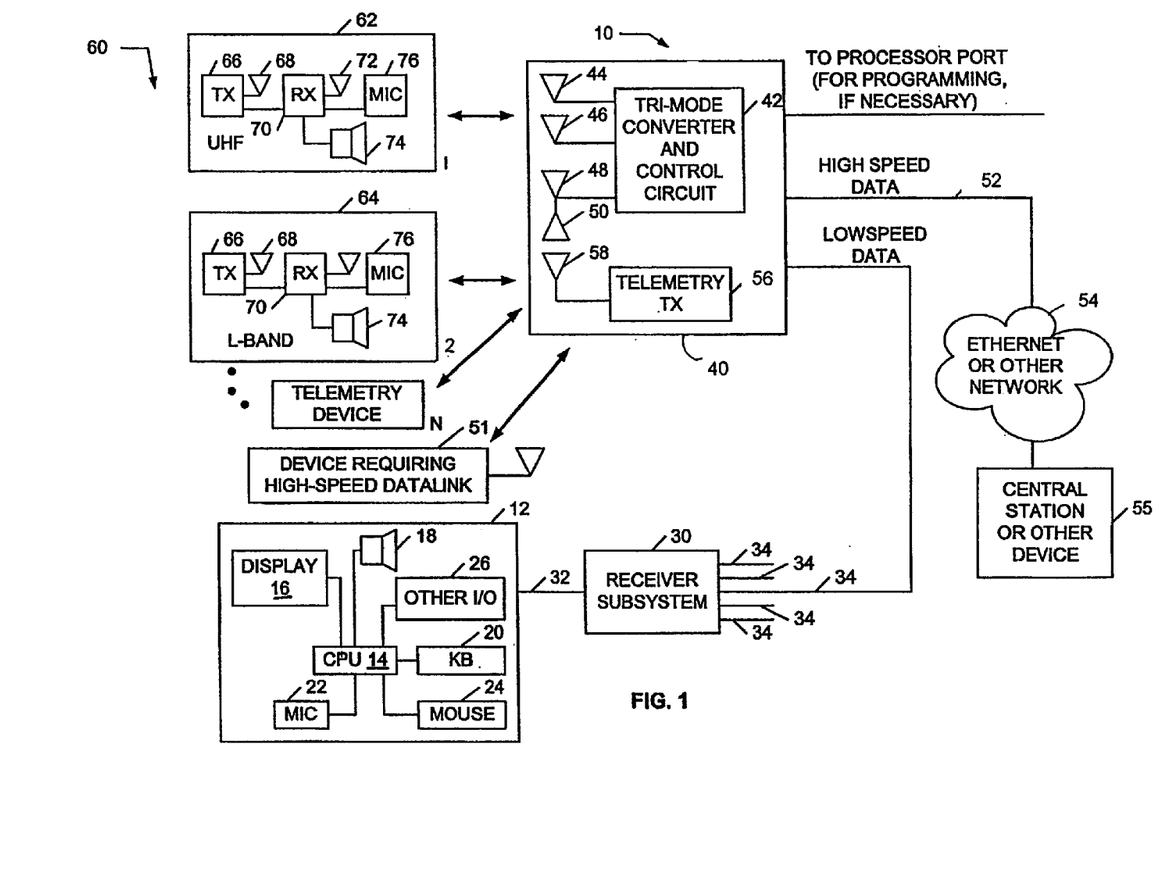
FIG. 1 is a block diagram of a tri-mode telemetry system embodying the invention.

FIG. 1 illustrates a tri-mode telemetry system 10 embodying the invention. The system 10 may include a central station 12. The central station 12 includes a processing unit or processor 14, which, in its most common form is a microprocessor.

The processor 14 is coupled to a display 16 and speaker 18 and may receive input from a keyboard 20, a microphone 22, or a mouse 24. The processor may transmit or receive additional outputs or inputs from other devices represented by block 26. The central station 12 is connected to a receiver subsystem 30 through a communication link 32. The receiver subsystem 30 includes a series of I/O ports 34 connected to a plurality of antennas or antenna units 40 (only one of which is shown). In use, the antenna units 40 may be spaced about a care unit to form an antenna array. While the number of units 40 may vary in any particular application, typically, each antenna unit 40 is identical.

The antenna unit 40 includes a converter and control circuit 42. The converter and control circuit 42 is coupled to a first RF antenna 44 tuned to receive signals having a frequency within a first communication or frequency band and a second antenna 46 tuned to receive signals having a frequency in a second communication or frequency band. In addition to the antennas 44 and 46, the antenna unit 40 includes a third antenna 48 tuned to a receive signal in a third communication band. Preferably, the signal in the third communication band is a digital signal. The digital signal may be a signal transmitted at a bit rate of 10 Mbps or higher. The third antenna 48 is associated with a fourth antenna 50 that is designed to transmit digital signals in the third communication band. The antennas 48 and 50 communicate with a data device 51 such as a patient monitoring system, telephony system, image transfer system, or other device that requires a relatively high-speed data link for acceptable operation (e.g., latency, jitter, and other characteristics at a level to support real-time or near real-time transmission of data). The antenna 48 receives information from the data device 51. The antenna 50 may be used to send commands, requests or other information to the data device 51. Information received by the antenna 48 may be transferred via a high-speed data link 52 to a network 54 such as an Ethernet network. A station 55 for monitoring the data received by the antenna 48 may be linked to the network 54.

The antenna unit 40 also includes an antenna transmitter circuit 56 connected to a transmitter antenna 58. The antenna transmitter circuit 56 generates an RF signal which may be used to transmit commands and information from the central station 12 to the telemetry transmitters discussed below.

The tri-mode telemetry system 10 includes a plurality of telemetry transmitters 60. The telemetry transmitters 60 may be one of two types. A first type 62 is designed to operate in a first frequency band (such as UHF) and a second type 64 is designed to operate in a second frequency band (such as L-band). As is known to those of ordinary skill in the art, the UHF telemetry band generally covers frequencies of about 470 MHz to about 668 MHz. The L-band generally covers signals having frequencies of about 1 GHz to about 2 GHz and, more particularly, about 1.4 GHz.

In use, each telemetry transmitter 60 is connected to a patient (not shown) via electrodes or connections suitable for measuring patient parameters (such as ECG electrodes). Once a telemetry transmitter 60 is connected to a patient, the patient's condition may be monitored. Due to the wireless nature of the telemetry transmitters, the patient's ability to ambulate throughout the care unit is unhindered by the transmitter. Each telemetry transmitter 60 (regardless of type) includes a transmitter circuit 66 connected to a transmitting antenna 68. The transmitter circuit 68 generates an RF carrier signal for transmitting patient and other data to the antenna unit 40. As noted previously, the frequency of the carrier signal is dependent on the type of telemetry transmitter used: type 62 (UHF) or type 64 (L-band).

Each telemetry transmitter also includes a receiver circuit 70 connected to a receiving antenna 72, and may include a speaker 74 and a microphone 76. The receiver circuit 70 includes support circuitry, power inputs, and common connections, as those of ordinary skill in the art would understand. The receiver circuit 70 also has a microprocessor input (not shown) connected to a microprocessor (not shown) of the telemetry transmitter. The microprocessor receives all physiological data and routes that data to the transmitter circuit 66. The microprocessor also processes the commands received by the receiver circuit 70 from the transmitter circuit 56 of the antenna unit 40.

Figure 2:
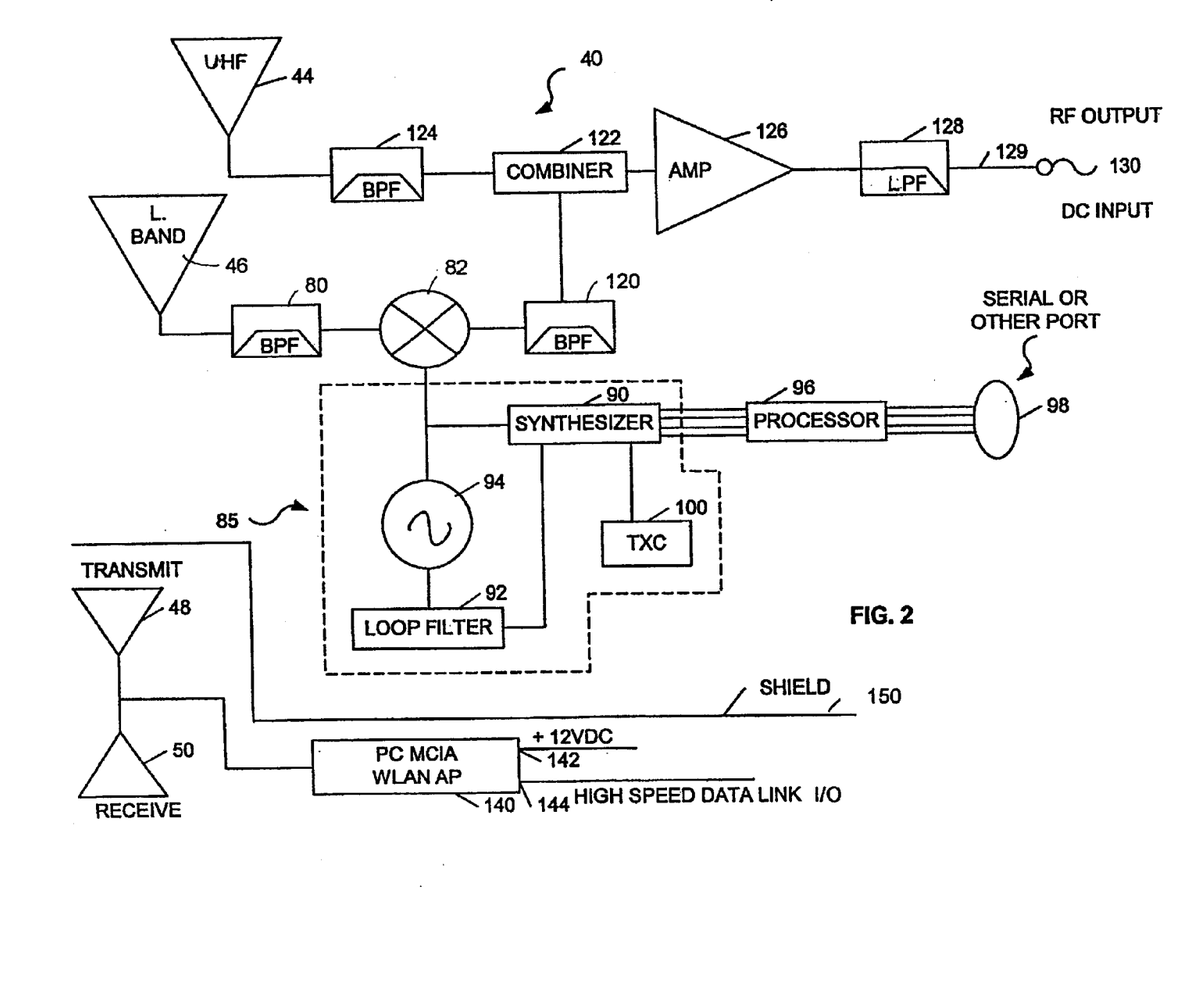
FIG. 2 is a block diagram of a converter and control unit and a wireless data access device that that may be used in the telemetry system of FIG. 1.

The converter and control circuit 42 of the antenna unit 40 is shown in greater detail in FIG. 2. The converter and control circuit 42 is designed such that both L-band and UHF signals may be processed by the receiver substation 30 and central station 12. The control circuit 42 receives signals from the UHF antenna 44. UHF antenna 44 receives signals from the UHF telemetry transmitter 62 in an available UHF channel. By way of example, one UHF channel is broadcast channel thirty-seven and this channel resides in the 6 MHz frequency band from 608 MHz to 614 MHz.

The control circuit 42 also receives signals from L-band antenna 46. L-band antenna 46 receives signals from the L-band telemetry transmitter 64 in an available L-band channel. The signal from the L-band antenna 46 is filtered by an L-band band pass filter 80 which removes signals outside of the L-band frequency range. The band-pass filter 80 also attenuates signals from a voltage-controlled oscillator (discussed below) to minimize emission signals from the voltage-controlled oscillator at the antenna 46. The L-band signals are delivered to a mixer 82, such as a JMS-5 mixer from Mini Circuits. The mixer 82 mixes the L-band signal with a frequency translation signal from a local oscillator 85 to produce a UHF band signal. The frequency translation signal is formed such that the UHF band signal generated by the mixer 82 resides in a different channel than the UHF signal received by the UHF antenna 44. Thus, in the case where the UHF antenna operates in broadcast channel thirty-seven, the signal generated by the mixer 82 would reside in a different channel, for example, broadcast channel forty.

Figure 3:
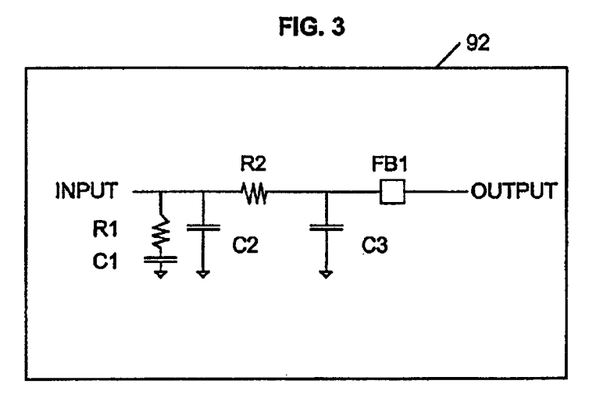
FIG. 3 is a circuit diagram of a filter suitable for use in a synthesizer local oscillator used in the converter and control unit.

The local oscillator 85 includes a synthesizer 90, such as the LMX2316 model from National Semiconductor. The synthesizer is coupled in a series (phase-lock) loop with a loop filter 92 and a voltage controlled oscillator 94. A loop filter suitable for use in the present invention is shown in FIG. 3. The voltage-controlled oscillator 94 may be one of several oscillators commercially available including those from Vari-L Company.

The synthesizer 90 is programmed by a microprocessor 96, which may be a commercially available processor such as a Microchip PIC16C620. The microprocessor 96 receives input through a port 98 such as a serial port. Information and commands delivered through the serial port 98 permit adjustment of the synthesizer frequency. The synthesizer 90 also receives input from a temperature controlled oscillator 100. The oscillator 100 provides the frequency reference for the synthesizer 90. The temperature controlled oscillator 100 may be implemented with commercially available oscillators such as an Oscillatek OSC-1B2 TCXO.

The output of the synthesizer 90 is delivered to the loop filter 92 which attenuates any reference spurs generated by the synthesizer 90, filters the noise in the loop, and controls the stability of the phase-lock loop. The voltage-controlled oscillator 94 oscillates at a frequency appropriate to achieve the desired translation frequency of the L-band signal so that it is down converted. The oscillation frequency of the voltage controlled oscillator 94 is set by the DC voltage received from the loop filter 92. The voltage-controlled oscillator produces a frequency translation signal that is delivered to the mixer 82. The frequency translation signal and the L-band signal from the antenna 46 are mixed in the mixer 82 and the resulting UHF signal is delivered to a band pass filter 120 which removes signals outside of the UHF frequency band. The filtered UHF signal is then delivered to a combiner 122, which may be a commercially available combiner such as a Mini Circuits JPS-2-900.

The combiner 122 also receives the UHF signal from the UHF antenna 44 as filtered by a band pass filter 124, which removes signals outside of the channel to which the antenna 44 is tuned. The combiner combines the UHF signals from the antenna 44 and mixer 82 and delivers them to an amplifier 126. After being amplified, the combined signals are filtered by a low pass filter 128, which removes harmonics of the two signals. The combined signals are output along a transmission line 129 to RF output node 130 (which also may serve as a DC input node) and are delivered to the receiver subsystem as described above.

Data signals to and from the data device 51 are processed in a card device 140. In one embodiment, the card device takes the form of a Personal Computer Memory Card International Association (PCMCIA) card configured to provide a wireless local area network (WLAN) access point (AP). In more general terms, the card device 140 acts as a wireless access device. The card device has a power input 142, which in the embodiment shown is coupled to a 12 V DC power supply. The card device also has a data input/output node 144.

Preferably, a shield 150 is positioned between the RF components (44, 46, 80, 82, 85, 120, 122, 124, 126, and 128) of the converter and control circuit 42 and the data transmission components of the circuit 42 (48, 50, and 140). The shield may take the form of a physical component such as a conductor or metal plate. Alternatively, sufficient shielding may be achieved by providing a predefined area of space between the RF components and data transmission components.

Figure 4:
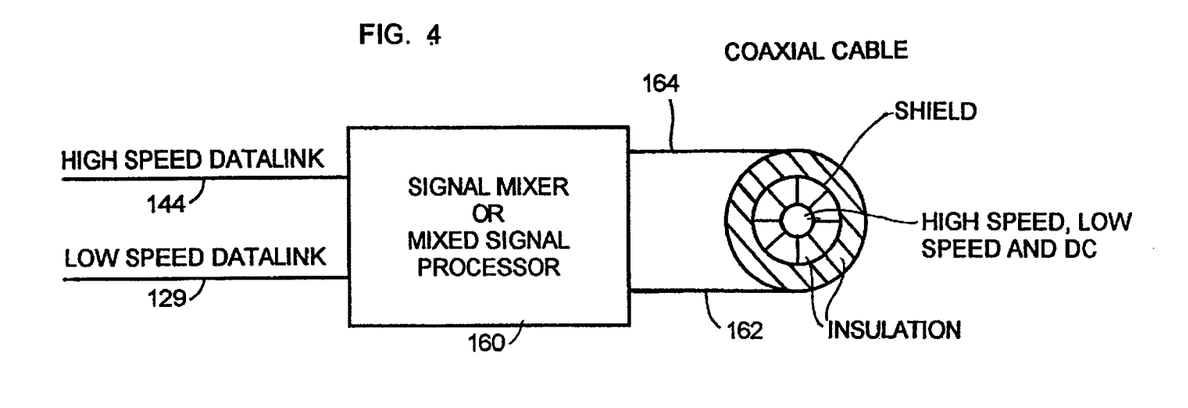
FIG. 4 is a block diagram of a mixed signal processor used to combine radio frequency telemetry signals and data signals on a single conductor.
Figure 5:
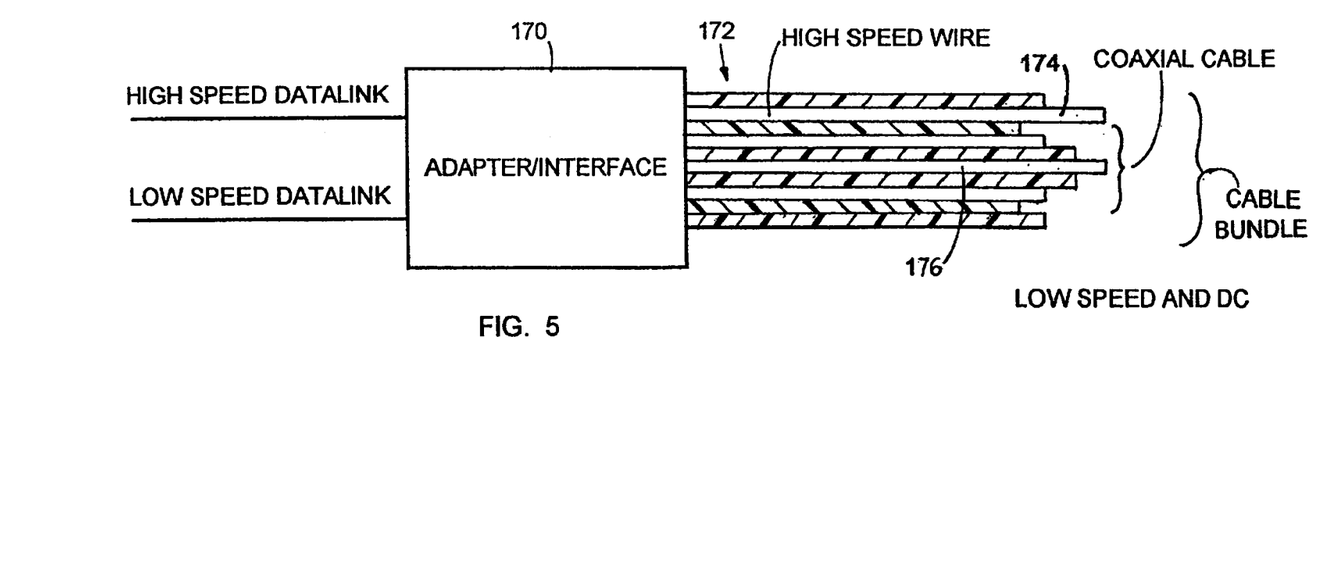
FIG. 5 is a block diagram of an adapter used to transfer radio frequency radio signals and data signals to a cable bundle.

FIGS. 4 and 5 illustrate additional features of the invention that may be implemented to reduce cabling requirements associated with transmitting both relatively low-speed telemetry data and relatively high-speed signals. FIG. 4 illustrates a mixed signal processor 160 that receives an RF output from link 129 and a data signal from output 144 of the card device 140. The mixed signal processor combines the RF signal from the link 129 with the data signal from the out put 144 and produces a signal output that is delivered to a center conductor 162 of a coaxial cable 164. The center conductor 162 may also carry a power signal such as a 12 V DC signal to power the amplifier 126 and the card device 140.

As shown in FIG. 1, the central station 12 and monitoring station 55 are used to monitor or otherwise control or process telemetry and relatively high-speed data, respectively. High speed data is routed to a standard wireline Ethernet network. If the cabling solution illustrated in FIG. 4 is implemented, a signal splitter or demultiplexer may be used to transfer the appropriate data to the central station 12 and monitoring station 55. Otherwise a unified monitoring station (not shown) operable to process both types of data could be implemented, as would be apparent to those of ordinary skill in the art.

FIG. 5 illustrates a cable bundle adapter 170. The adapter 170 receives a cable bundle 172 that has a first transmission line or conductor 174. The conductor 174 carries high-speed data signals. An exemplary conductor suitable for use in the invention is a 10Base-T line or cable or other wire or cable having a similar or better data capacity. The cable bundle 172 also includes a second conductor 176 that carries low-speed data. The second conductor 176 may take the form of a coaxial cable in which case the center conductor of the coaxial cable is used to transmit relatively low speed RF data. The center conductor may also be used to provide a power signal for the amplifier 126 and card device 140.

As can be seen from the above, the present invention provides a tri-mode telemetry system for collecting information from telemetry transmitters worn by patients and transmitting other data that requires relatively high speed data links.

Various features and advantages of the invention are set forth in the following

What is claimed is:

1. A tri-mode telemetry system comprising:
   a first antenna tuned to receive a signal having a frequency in a first communication band;
   a second antenna tuned to receive a signal having a frequency in a second communication band;
   a down converter for producing a frequency translation signal;
   a mixer coupled to the second antenna and to the down converter such that the mixer uses the signal received by the second antenna and the frequency translation signal to produce a signal having a frequency in the first communication band;
   a combiner for combining the signal having a frequency in the first communication band with the signal received by the first antenna and operable to produce an output signal;
   a third antenna designed to receive a signal in a third communication band;
   a wireless access device coupled to the third antenna and operable to produce an output signal; and
   a shield between the third and the first and second antennas.

2. A tri-mode telemetry system as set forth in claim 1, wherein the shield is a predefined area of space.

3. A tri-mode telemetry system as set forth in claim 1, wherein the shield is a metal plate.

4. A tri-mode telemetry system as set forth in claim 1, wherein the first communication band is the UHF band and the second communication band is the L-band.

5. A tri-mode telemetry system as set forth in claim 1, further comprising a cable bundle adapter coupled to the combiner and the wireless access device, the adapter operable to accept a cable bundle having a first conductor operable to transmit data in the first communication band and a second conductor operable to transmit data in the third communication band.

6. A tri-mode telemetry system as set forth in claim 1, further comprising a mixed signal processor coupled to the combiner and the wireless access device, the mixed signal processor operable to mix the output signal of the combiner with the output signal of the wireless access device.

7. A tri-mode telemetry system as set forth in claim 1, wherein the wireless access device is a card device.

8. A tri-mode telemetry system as set forth in claim 1, wherein the down converter further comprises:
   an oscillator;
   a synthesizer; and
   a filter, the oscillator, the synthesizer, and the filter coupled in a series loop, the synthesizer coupled to a temperature controlled oscillator and a processor having an input.

9. A tri-mode telemetry system set forth in claim 1, further comprising:
   a first band pass filter coupled between the first antenna and the combiner and for blocking signals having frequencies outside a predetermined channel in the first RF band;
   a second band pass filter coupled between the second antenna and the mixer and for blocking signals having frequencies outside the second RF band; and
   a third band pass filter coupled between the mixer and the combiner and for blocking signals outside the first RF band.

10. A tri-mode telemetry system as set forth in claim 4, further comprising:
    an amplifier coupled to the combiner; and
    a low-pass filter coupled to the amplifier.

11. A tri-mode telemetry system comprising:
    a first telemetry transmitter for acquiring patient data and transmitting the patient data in a first signal having a frequency in a first RF band;
    a second telemetry transmitter for acquiring patient data and transmitting the patient data in a second signal having a frequency in a second RF band;
    a communication device that generates a third signal in a communication band;
    an antenna array for receiving the first and second signals from the first and second telemetry transmitters and the third signal, the antenna array including
    a first antenna tuned to receive the first signal,
    a second antenna tuned to receive the second signal,
    a down converter for producing a frequency translation signal,
    a mixer coupled to the second antenna and to the down converter, the mixer for using the signal received by the second antenna and the frequency translation signal to produce a signal having a frequency in the first RF band; and
    a combiner for combining the signal having a frequency in the first RF band with the signal received by the first antenna;
    a third antenna tuned to receive the third signal,
    a wireless access device coupled to the third antenna and operable to produce an output signal;
    a shield positioned between the third antenna and wireless access device and the first and second antennas;
    a receiver subsystem coupled to the combiner; and
    a central station coupled to the receiver subsystem and for receiving the patient data.

12. A tri-mode telemetry system as set forth in claim 11, wherein the shield is a predefined area of space.

13. A tri-mode telemetry system as set forth in claim 11, wherein the shield is a conductor.

14. A tri-mode telemetry system as set forth in claim 11, wherein the first RF band is the UHF band and the second RF band is the L-band.

15. A tri-mode telemetry system as set forth in claim 11, further comprising a cable bundle adapter coupled to the combiner and the wireless access device, the adapter operable to accept a cable bundle having a first conductor operable to transmit data in the first communication band and a second conductor operable to transmit data in the third communication band.

16. A tri-mode telemetry system as set forth in claim 11, further comprising a mixed signal processor coupled to the combiner and the wireless access device, the mixed signal processor operable to modulate the output signal of the combiner and mix the modulated signal with the output signal of the wireless access device.

17. A tri-mode telemetry system as set forth in claim 11, wherein the wireless access device is a computer card.

18. A tri-mode telemetry system as set forth in claim 11, wherein the down converter further comprises:
    an oscillator;
    a synthesizer; and
    a filter, the oscillator, the synthesizer, and the filter coupled in a series loop, the synthesizer coupled to a temperature controlled oscillator and a processor having an input.

19. A tri-mode telemetry system set forth in claim 11, further comprising:
    a first band pass filter coupled between the first antenna and the combiner and for blocking signals having frequencies outside a predetermined channel in the first RF band;
    a second band pass filter coupled between the second antenna and the mixer and for blocking signals having frequencies outside the second RF band; and
    a third band pass filter coupled between the mixer and the combiner and for blocking signals outside the first RF band.

20. A tri-mode telemetry system as set forth in claim 11, further comprising
    an amplifier coupled to the combiner; and
    a low-pass filter coupled to the amplifier.

21. A tri-mode telemetry system comprising:
    a first antenna tuned to receive a signal having a frequency in a first communication band;
    a combiner coupled to the first antenna;
    a second antenna tuned to receive a signal having a frequency in a second communication band;
    a mixer coupled to the second antenna and the combiner;
    an oscillator coupled to the mixer and having an output, and wherein the mixer is configured to mix signals received from the second antenna with the output of the oscillator to produce a signal within the first frequency band;
    a third antenna operable to receive signals in a third communication band;
    a wireless access device coupled to the third antenna and operable to produce and output; and
    a shield positioned between the third antenna and wireless access device and the first and second antennas, combiner, mixer, and oscillator.

22. A tri-mode telemetry system as set forth in claim 21, wherein the shield is a predefined area of space.

23. tri-mode telemetry system as set forth in claim 21, wherein the shield is a metal plate.

24. A tri-mode telemetry system as set forth in claim 21, wherein the first antenna is tuned to receive a signal in a first channel within the first communication band, the second antenna is tuned to receive a signal in a first channel within the second communication band, and the mixer is operable to produce a signal in a second channel within the first communication band.

25. A tri-mode telemetry system as set forth in claim 21, wherein the first communication band is the UHF band and the second communication band is the L-band.

26. A tri-mode telemetry system as set forth in claim 21, further comprising:
    a first telemetry transmitter for acquiring patient data and transmitting the patient data in a first signal having a frequency in the first communication band;
    a second telemetry transmitter for acquiring patient data and transmitting the patient data in a second signal having a frequency in the second communication band;
    a receiver subsystem coupled to the combiner; and
    a central station coupled to the receiver subsystem and for receiving the patient data, wherein the first antenna is tuned to receive the first signal from the first transmitter and the second antenna is tuned to receive the second signal from the second transmitter.

27. A tri-mode telemetry system as set forth in claim 26, further comprising:
    a synthesizer; and
    a filter, such that the oscillator, the synthesizer, and the filter are coupled in a series loop.

28. A tri-mode telemetry system as set forth in claim 27, further comprising:
    a processor coupled to the synthesizer and having an input; and
    a temperature controlled oscillator coupled to the synthesizer.

29. A tri-mode telemetry system as set forth in claim 21, further comprising an adapter coupled to the combiner and the wireless access device, the adapter operable to accept a cable bundle having a first conductor operable to transmit data in the first communication band and a second conductor operable to transmit data in the third communication band.

30. A tri-mode telemetry system as set forth in claim 21, further comprising a mixed signal processor coupled to the combiner and the wireless access device, the mixed signal processor operable to modulate the output signal of the combiner and mix the modulated signal with the output signal of the wireless access device.

31. A method of monitoring patients in a care unit, the method comprising:
    acquiring a patient data signal from a first transmitter that operates in a first communication band;
    acquiring a patient data signal from a second transmitter that operates in a second communication band;
    converting the patient data signal from the second transmitter to a third signal in the first communication band;
    combining the first and third signals;
    acquiring a data signal from a first data device that operates in a third communication band; and
    delivering the combined first and second signals and the data signal to a wiring system.

32. A method as set forth in claim 31, wherein the act of acquiring a patient data signal from a first transmitter is accomplished using a first antenna tuned to receive a signal in a first channel within the first communication band, and the act of acquiring a patient data signal from a second transmitter is accomplished using a second antenna tuned to receive a signal in a first channel within the second communication band.

33. A method as set forth in claim 31, wherein the act of converting the patient data signal from the second transmitter to a third signal includes mixing the patient data signal from the second transmitter with a frequency translation signal from a local oscillator.

34. A method as set forth in claim 31, further comprising filtering the combined first and third signals prior to delivering the combined first and third signals to a receiver.

35. A method as set forth in claim 31, further comprising filtering the patient data signal from a first transmitter to remove frequencies outside a first channel in the first communication band.

36. A method as set forth in claim 31, further comprising filtering the patient data signal from a second transmitter to remove frequencies outside a first channel in the second communication band.

37. A method as set forth in claim 31, further comprising filtering the third signal to remove frequencies outside of the first communication band.

38. A method as set forth in claim 31, further comprising processing the first and third signals at a central station.

39. A method as set forth in claim 31, further comprising delivering the combined first and second signals and the data signal to an adapter.

40. A method as set forth in claim 31, further comprising delivering the combined first and second signals and the data signal to a mixed signal processor and modulating the combined first and second signal in the mixed signal processor.

* * * * *